(12) United States Patent
Chi et al.

(10) Patent No.: US 7,566,773 B2
(45) Date of Patent: Jul. 28, 2009

(54) PHOTOLABILE COMPOUND AND SUBSTRATE FOR OLIGOMER PROBE ARRAY WITH THE SAME

(75) Inventors: Sung-min Chi, Hwaseong-si (KR);
Jung-hwan Hah, Hwaseong-si (KR);
Kyoung-seon Kim, Suwon-si (KR);
Won-sun Kim, Suwon-si (KR);
Sang-jun Choi, Seoul (KR);
Man-hyoung Ryoo, Hwaseong-si (KR)

(73) Assignee: Samsung Electronics Co., Ltd., Suwon-si, Gyeonggi-Do (KR)

( * ) Notice: Subject to any disclaimer, the term of this patent is extended or adjusted under 35 U.S.C. 154(b) by 312 days.

(21) Appl. No.: 11/686,626

(22) Filed: Mar. 15, 2007

(65) Prior Publication Data

US 2008/0057489 A1 Mar. 6, 2008

(30) Foreign Application Priority Data

Aug. 7, 2006 (KR) .................... 10-2006-0074355

(51) Int. Cl.
*C07H 19/00* (2006.01)
*C07H 21/00* (2006.01)
(52) U.S. Cl. .................... 536/22.1; 536/24.3; 536/25.32
(58) Field of Classification Search ...................... None
See application file for complete search history.

(56) References Cited

U.S. PATENT DOCUMENTS

| | | |
|---|---|---|
| 6,673,544 B1 | 1/2004 | Beier et al. |
| 6,750,335 B2 | 6/2004 | Pfleiderer et al. |
| 2002/0053508 A1 | 5/2002 | Stengele et al. |
| 2002/0146737 A1 | 10/2002 | Pfleiderer et al. |
| 2003/0040618 A1 | 2/2003 | Barone et al. |
| 2004/0116680 A1 | 6/2004 | Beier |

OTHER PUBLICATIONS

Korean Office Action.

*Primary Examiner*—Patrick T Lewis
(74) *Attorney, Agent, or Firm*—F. Chau & Associates

(57) ABSTRACT

Provided is a substrate for an oligomer probe array to which a photolabile material having an acetylene derivative is directly attached or attached via a linker.

9 Claims, 3 Drawing Sheets

PHOTOLABILE COMPOUND AND SUBSTRATE FOR OLIGOMER PROBE ARRAY WITH THE SAME

CROSS REFERENCE TO RELATED APPLICATION

This application claims priority from Korean Patent Application No. 10-2006-0074355 filed on Aug. 7, 2006 in the Korean Intellectual Property Office, the contents of which are herein incorporated by reference in their entirety.

BACKGROUND OF THE INVENTION

1. Field of the Invention

The present disclosure is directed to a photolabile compound and a substrate for an oligomer probe array to which the photolabile compound is attached.

2. Description of the Related Art

The term "oligomer probe array" refers to an array in which an oligomer probe is densely arrayed onto a solid support such as a silicon wafer substrate.

As a method of forming an oligomer probe array by accumulating various biopolymers on the oligomer probe array, various methods are known and even at present new methods have been proposed.

The oligomer probe array can be produced, for example, by a method in which protective groups in a specific area are removed by light irradiation on the substrate to which functional groups protected by photolabile protective groups are fixed, to expose the functional groups, and an oligomer probe such as an oligonucleotide, a polypeptide or a peptide nucleic acid (PNA), is attached to a substrate. Further, the oligomer probe array can be produced by a method in which monomers are in-situ synthesized using photolithography or a method in which the previously synthesized oligomer probe is attached to a substrate using a process such as spotting.

The photolabile protective groups protect reactive functional groups until they are exposed to constant light. Exemplary photolabile protective groups that are currently known include nitroveratryloxycarbonyl (NVOC), nitropiperonyloxycarbonyl (NPOC), α-methylnitroveratryloxycarbonyl (MeNVOC), 1-pyrenylmethyloxycarbonyl (PyMOC), α-methylnitropiperonyloxycarbonyl (MeNPOC, 2-(3,4-methylenedioxy-2-nitrophenyl)propyloxycarbonyl), dinitrophenylalkylsulfonyl and 2-(2-nitrophenyl)propyloxycarbonyl (NPPOC).

The photolabile protective groups may be used in the production of oligomer probe arrays and the photolytic degradation rate may be varied depending on the kinds of the photolabile protective groups. Therefore, for the purpose of improving the total reaction yield, efforts have been continued to develop a photolabile compound capable of providing photolabile protective groups suitable for the production of oligomer probe arrays.

SUMMARY OF THE INVENTION

An exemplary embodiment of the present invention provides a novel photolabile compound capable of increased photolytic degradation rate.

Another exemplary embodiment of the present invention provides a substrate for an oligomer probe array to which the photolabile compound is attached.

According to an aspect of the present invention, there is provided a photolabile compound represented by the following formula:

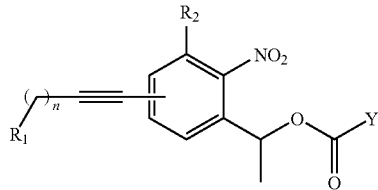

wherein
$R_1$ is a methyl group ($CH_3$), an amino group ($NH_2$), a hydroxyl group (OH), an acetic ester group ($CH_3COO$—), a phenyl group, a diphenyl group, a trimethylsilyl group (TMS), a cyanide group (CN), an azide group, a sulfur atom, a cycloalkyl group, a cycloalkenyl group or a heterocyclic group);

n is an integer from 1 to 8;

$R_2$ is a hydrogen atom or alkyl derivative; and

Y is a halogen atom, a hydroxyl group, or a moiety represented by one of the following formulae:

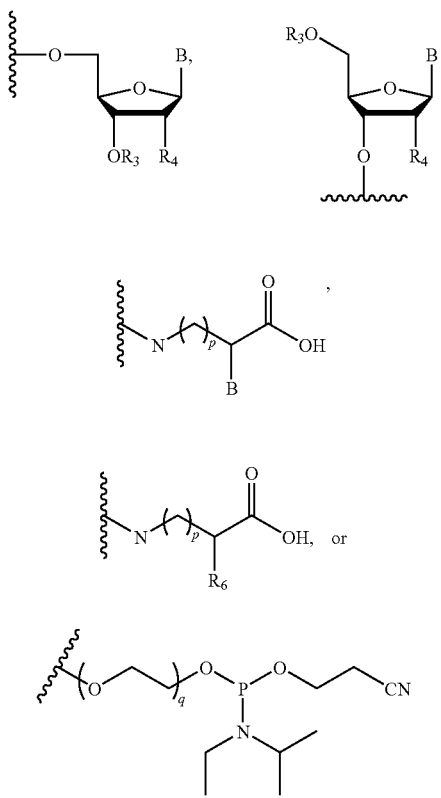

wherein
B is adenine, cytosine, guanine, thymine or uracil;

$R_3$ is a hydrogen atom, an amino group, an alkyl group or a phosphine group;

$R_4$ is a hydrogen atom, a hydroxyl group, —$OR_5$ or —$SR_5$ wherein $R_5$ is an alkyl group, an alkenyl group, an acetal group or a silyl ether group;

$R_6$ is an alkyl group, a phenyl group, or a sulfur atom;

p is an integer from 0 to 5; and q is an integer from 0 to 10.

According to another aspect of the present invention, there is provided a substrate for an oligomer probe array to which a material may be directly attached or attached via a linker, the material being represented by the following formula:

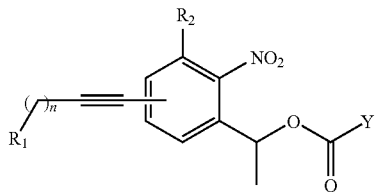

wherein $R_1$ is a methyl group, an amino group, a hydroxyl group, an acetic group, a phenyl group, a diphenyl group, a trimethylsilyl group, a cyanide group, an azide group, a sulfur atom, a cycloalkyl group, a cycloalkenyl group or a heterocyclic group;

n is an integer from 1 to 8;

$R_2$ is a hydrogen atom or an alkyl derivative; and

Y is a halogen atom, a hydroxyl group, or

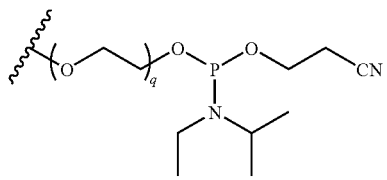

wherein q is an integer from 0 to 10.

BRIEF DESCRIPTION OF THE DRAWINGS

The above and other features of the present invention will become more apparent by describing in detail preferred embodiments thereof with reference to the attached drawings.

DETAILED DESCRIPTION OF THE EXEMPLARY EMBODIMENTS

Figure 1:
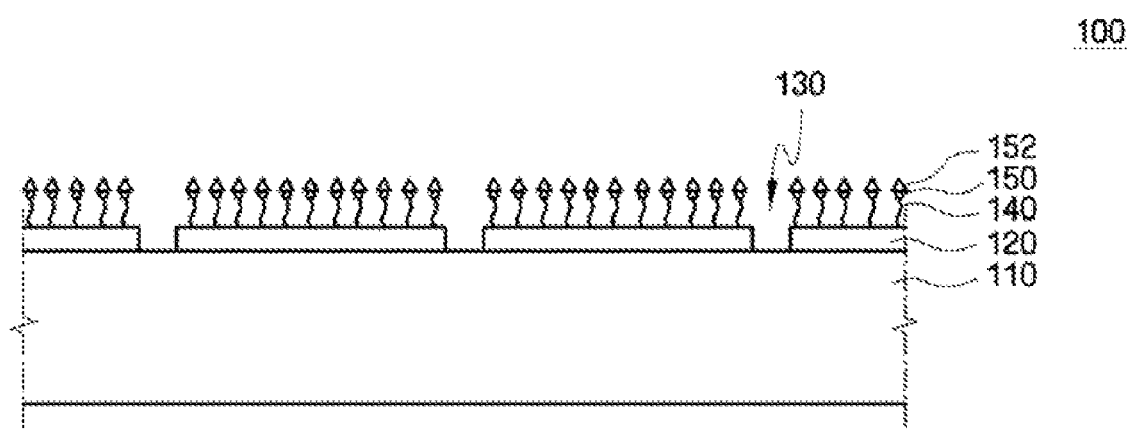
FIGS. 1 to 3 are each a cross sectional view illustrating a substrate for an oligomer probe array to which a photolabile compound is directly attached or attached via a linker, according to an embodiment of the present invention.

Features of embodiments of the present invention and methods of accomplishing the same may be understood more readily by reference to the following detailed description of exemplary embodiments and the accompanying drawings. Embodiments of the invention may, however, be embodied in many different forms and should not be construed as being limited to the embodiments set forth herein.

A photolabile compound according to at least one embodiment of the present invention may be represented by the following formula:

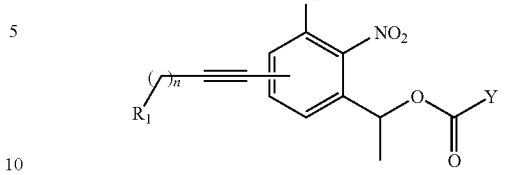

wherein $R_1$ is a methyl group ($CH_3$), an amino group ($NH_2$), a hydroxyl group (OH), an acetic ester group ($CH_3COO$—), a phenyl group, a diphenyl group, a trimethylsilyl group (TMS), a cyanide group (CN), an azide group, a sulfur atom, a cycloalkyl group, a cycloalkenyl group, or a heterocyclic group;

n is an integer of 1 to 8; and $R_2$ is a hydrogen atom or an alkyl derivative.

A moiety in which Y is removed from the formula, may be referred to as a photolabile protective group. The photolabile protective group may be referred to as a group that is attached to a reactive functional group so that a chemical reaction does not occur until it is removed by exposure to UV radiation or visible light. A chemical reaction occurs when photolabile protective groups are removed and the reactive functional groups are exposed, a process referred to as deprotection. A compound containing photolabile protective groups may be referred to as a photolabile compound.

The photolabile protective groups of the photolabile compound according to an embodiment of the invention have a fast deprotection reaction rate and thus have a short half-life during irradiation. Therefore, when the photolabile compound according to an embodiment of the present invention is used in the production of a oligomer probe array, the total reaction yield can be increased.

In an embodiment of the present invention, Y in the formula may be a halogen atom or a hydroxyl group. If Y is a halogen atom or a hydroxyl group, it may be attached to nucleoside, peptide nucleic acid, a linker or the like to constitute a monomer, a linker or the like, which is used in the production of an oligomer probe.

An embodiment having photolabile protective groups may include one in which Y is a nucleoside or a nucleotide.

Y in another embodiment of the present invention may be specifically

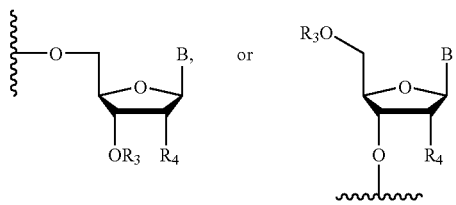

wherein B is adenine, cytosine, guanine, thymine or uracil;

$R_3$ is a hydrogen atom, an amino group, an alkyl group or a phosphine group; and $R_4$ is a hydrogen atom, a hydroxyl group, —$OR_5$ or —$SR_5$ wherein $R_5$ is an alkyl group, an alkenyl group, an acetal group or a silyl ether group.

If the photolabile compound according to an embodiment of the present invention is a nucleoside and a derivative thereof, $R_1$ may include specifically trimethylsilyl, methanol, cyclohexyl, cyclohexenyl, phenyl, naphthalenyl or thiophenyl.

The photolabile compound may also be a photolabile compound wherein $R_3$ is a hydrogen atom or a phosphite amide group and the OH group at the 3' or 5' position of ribofuranose and deoxyrifofuranose may be free or protected by protective groups. According to an embodiment of the invention, the $R_3$ of a photolabile compound is a phosphite amide group of the following formula:

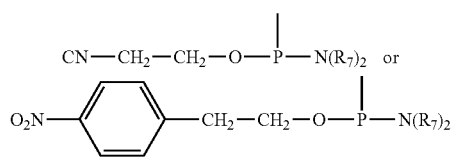

wherein $R_7$'s may be the same or different from each other and are independently a linear or branched alkyl radical having 1 to 4 carbon atoms.

$R_4$ in the photolabile compound may be an O-methyl radical, O-ethyl radical, an O-allyl radical, an O-tetrahydropyranyl radical, an O-methoxytetrahydropyranyl radical or an O-t-butyldimethylsilyl radical.

The nucleoside and nucleotide may contain not only the known purine and pyrimidine bases but also methylated purine or pyrimidine and acylated purine or pyrimidine. Further, the nucleoside and nucleotide may contain not only the conventional ribofuranose and deoxyribofuranose but also a modified sugar in which one or more hydroxyl groups are substituted by a halogen atom or an aliphatic group or a functional group such as ether is linked thereto. The photolabile protective groups may be linked to these nucleoside and nucleotide, and derivatives thereof to form a photolabile compound.

Y in at least one other embodiment of the present invention may be

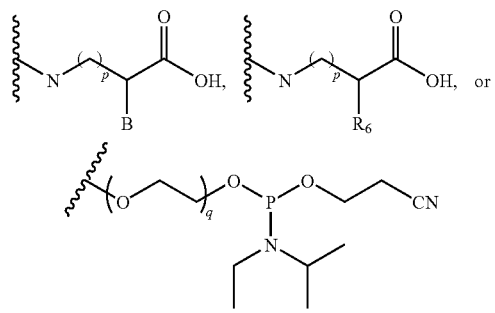

wherein
B is adenine, cytosine, guanine, thymine or uracil;
$R_6$ is an alkyl group, a phenyl group or a sulfur atom;
p is an integer of 0 to 5; and
q is an integer of 0 to 10, preferably 3 to 10.

The above-mentioned photolabile compound may be a linker molecule inserted between an oligomer probe and a substrate. The linker may provide a spatial margin required for the hybridization of oligomer probe and a sample in an oligomer probe array. Specifically, the linker may be used for providing the optimum length between the synthesized oligomer probe and the substrate.

Hereinafter, the above-mentioned substrate for an oligomer probe array to which a photolabile compound is attached, will be explained.

Figure 2:
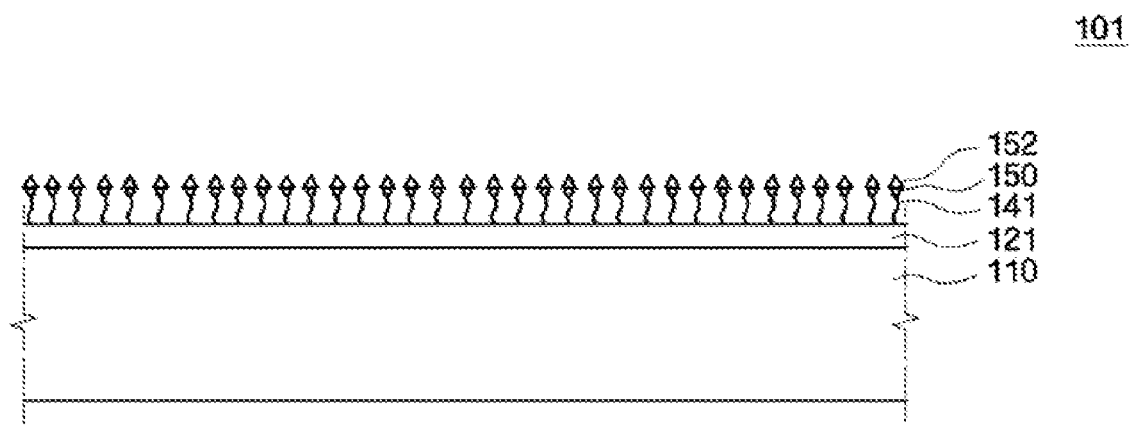
Figure 3:
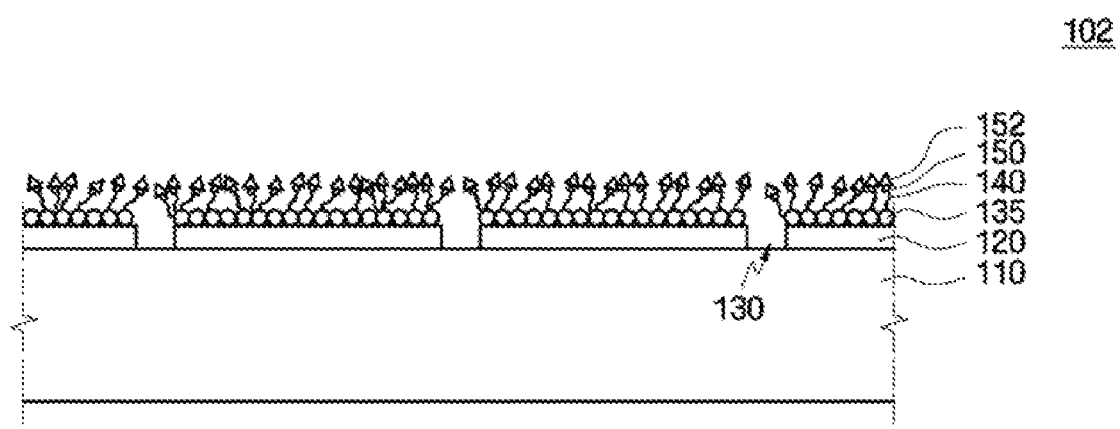

FIGS. 1 to 3 are each a cross-sectional view illustrating a substrate for an oligomer probe array to which a photolabile compound is directly attached or attached via a linker, according to at least one embodiment of the present invention.

The substrate for an oligomer probe array refers to a substrate for the production of an oligomer probe array. The substrate for an oligomer probe array 100, 101 or 102 refers to a substrate for an oligomer probe array to which a material is directly attached or attached via a linker, the material being represented by the following formula:

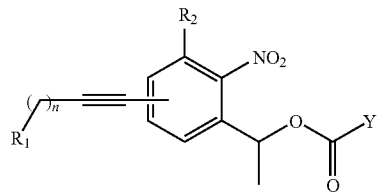

wherein
$R_1$ is a methyl group, an amino group, a hydroxyl group, an acetic ester group, a phenyl group, a diphenyl group, a trimethylsilyl group, a cyanide group, an azide group, a sulfur atom, a cycloalkyl group, a cycloalkenyl group or a heterocyclic group;
n is an integer of 1 to 8;
$R_2$ is a hydrogen atom or an alkyl derivative; and
Y is a halogen atom, a hydroxyl group, or

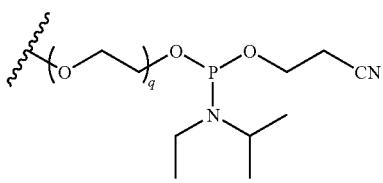

wherein q is an integer from 0 to 10.

The term "oligomer probe array" refers to an array in which an oligomer probe is high-density arrayed onto a solid support such as a silicon wafer substrate. The oligomer probe refers to a polymer having molecular weight of about 1000 or less, comprising two or more covalently-linked monomers, but the molecular weight is not limited to the above value. The oligomer probe may contain 2 to 500 monomers, preferably 5 to 30 monomers. The monomer may be a nucleoside, a nucleotide, an amino acid, a peptide or the like depending on the type of the probe. The oligomer probe may be previously synthesized or synthesized through an in-situ photolithography process in an active state.

The substrate 110 may be formed of a material capable of minimizing or becoming substantially free of the undesired non-specific binding during hybridization. Further, the substrate 110 may be formed of a material transparent to visible light and/or UV radiation. The substrate may be a flexible or rigid substrate. The flexible substrate may be a membrane such as nylon and nitrocellulose or a plastic film. The rigid substrate may be a silicon substrate or a transparent glass substrate such as soda-lime glass. When the silicon substrate or transparent glass substrate is used, non-specific binding rarely occurs during hybridization. Further, when the transparent glass substrate is used, it is useful in the detection of a fluorescent material since it is transparent to visible light and/or UV radiation. Known production processes of various thin films and photolithography processes, which have been previously stably established and applied in the production process of a semiconductor device or the production process of an LCD panel, can be applied to the production of the silicon substrate or transparent glass substrate.

Referring to FIGS. 1 to 3, the substrate for an oligomer probe array 100, 101 or 102 may be a substrate to which the photolabile protective groups 152 of the above-mentioned photolabile compound are attached via linkers (linker molecules) 140. The linkers 140 may provide a spatial margin required for the hybridization of an oligomer probe and a sample in an oligomer probe array. Specifically, the linkers may be used for providing the optimum length between the synthesized oligomer probe and the substrate. The linkers 140 may be silane linkers or nano particles.

Referring to FIG. 1, probe cell active regions 120 may be formed on the surface of the substrate 110, the linkers 140 may be inserted in each probe cell active region 120, and then the photolabile protective group 152 of the photolabile compound may be attached to functional groups 150 of the linkers 140. Regions surrounding the probe cell active regions 120, in which the linkers 140 are not attached thereto, are referred to as probe cell isolation regions 130.

The probe cell active regions 120 are preferably formed of a material that remains substantially stable without hydrolysis under conditions for hybridization analysis, for example, during the contact with a phosphate or TRIS buffer at pH 6 to 9. Therefore, the probe cell active region 120 may be formed of a silicon oxide film such as a spin-on siloxane film, a PE-TEOS film an HDP oxide film or P—SiH$_4$ oxide film and a thermal oxide film, silicate such as hafnium silicate and zirconium silicate, a silicon nitride film, a metal oxynitride film such as a silicon oxynitride film, a hafnium oxynitride film and a zirconium oxynitride film, a metal oxide film such as a titanium oxide film, a tantalum oxide film, an aluminum oxide film, a hafnium oxide film, a zirconium oxide film and ITO, polyimide, polyamine, a metal such as gold, silver, copper and palladium, or a polymer such as polystyrene, polyacrylic acid and polyvinyl. The probe cell active region 120 may be formed of a material that has been stably applied in the production process of a semiconductor device or the production process of an LCD panel, which it may be suitable in terms of the production process.

Referring to FIG. 2, a fixation layer 121 may be formed on the surface of the substrate 110, the linkers 141 may be inserted in the fixation layer 121, and then the photolabile protective group 152 of the photolabile compound may be attached to functional groups 150 of the linkers 141.

Referring to FIG. 3, probe cell active regions 120 may be formed on the surface of the substrate 110, nano particles 135 may be inserted in each probe cell active region 120, the linkers 140 may be inserted in the nano particles 135, and then the photolabile protective groups 152 of the photolabile compound may be attached to functional groups 150 of the linkers 140.

When the photolabile compound containing photolabile protective groups 152 inherently has a function as a linker, the formation of the linkers 140 may be omitted and the photolabile compound may be directly attached to the probe cell active regions 120, fixation layer 121 or nano particles 135.

The photolabile protective groups 152 of the photolabile compound in the substrate for an oligomer probe array 100, 101 or 102 according to the embodiment of the present invention have a fast deprotection reaction rate and thus have a short half-life during irradiation. Therefore, when the substrate for an oligomer probe array 100, 101 or 102 according to embodiments of the present invention is used in the production of an oligomer probe array, the total reaction yield can be increased.

Hereinafter, a method for producing the photolabile compound according to embodiments of the present invention will be described.

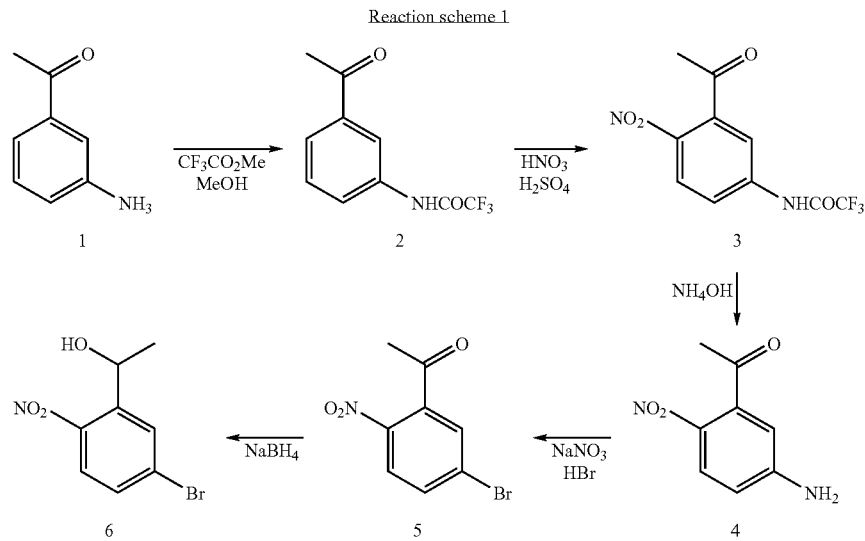

Reaction scheme 1

First, a compound having halonitrophenyl may be synthesized in accordance with the reaction scheme 1.

3'-Aminoacetophenone (1) as a starting material is reacted with methyl trifluoroacetate in a methanol solvent to synthesize a protecting compound (2) and thereafter subjected to nitrification by adding sulfuric acid and nitric acid. Then, the resulting compound (3) is subjected to deprotection by adding ammonia to obtain a compound (4) and then subjected to a Sandmeyer reaction to obtain a compound (5). Subsequently, the resulting compound (5) is reacted with sodium borohydride to obtain a compound (6). The compound obtained in each step is separated using silica gel column chromatography.

Then, an acetylene derivative may be formed in accordance with the reaction scheme 2.

Reaction scheme 2

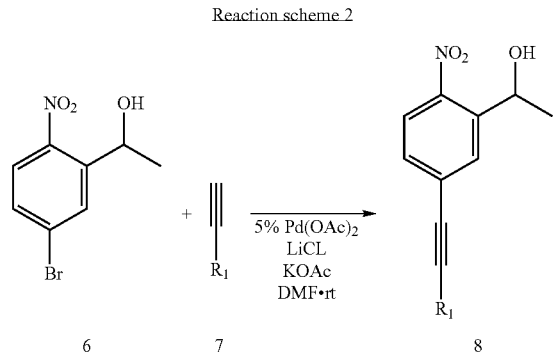

A derivative (8) to which various functional groups are attached, may be synthesized from compounds (6) (from Reaction scheme 1) and (7) in the presence of a palladium catalyst. In particular, various derivatives (8) may be synthesized using the acetylene derivative.

Next, the alcohol (8) formed in the above process may be reacted with a phosgene derivative (9) to obtain a photolabile compound (10) containing oxycarbonyl chloride as shown in the reaction scheme 3 below. The Y in the compound represented by the formula is a halogen atom, particularly a chlorine atom.

Reaction scheme 3

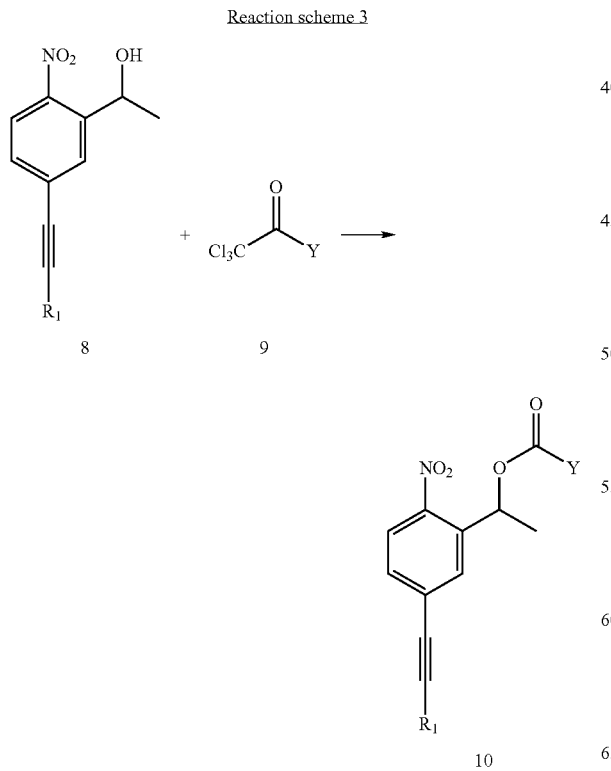

The reaction may be carried out in a nonpolar organic solvent at −20° C. to +25° C. In addition to phosgene, diphosgene (chloroformic acid trichloromethyl ester) or triphosgene (bistrichloromethyl carbonate) may be used as the phosgene derivative.

Hereinafter, a method for producing the photolabile compound wherein Y in the formula is

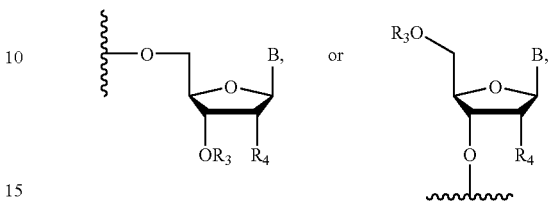

that is, nucleosides to which photolabile protective groups are attached, via a reaction scheme 4, will be described.

Reaction scheme 4

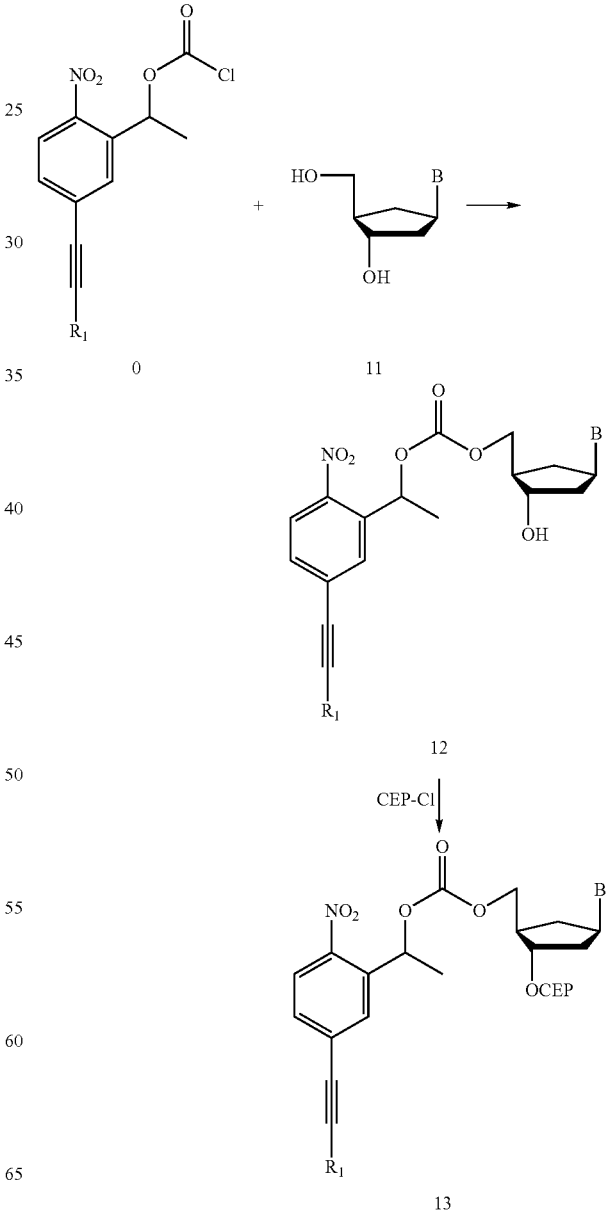

A nucleoside (12) having photolabile protective groups of the formula 1 is synthesized from photolabile compound (10) containing oxycarbonyl chloride and nucleoside (11). Thereafter, any excess phosgene derivative and the solvent are first distilled off under vacuum and then chlorocarbonic acid ester is reacted with the nucleoside having photolabile protective groups (12).

The reaction of the chlorocarbonic acid ester and the nucleoside having photolabile protective groups (12) may be carried out in a solvent mixture consisting of dichloromethane and a polar organic solvent, optionally in the presence of a base, at −60 to +25° C. DMF or pyridine may be used as the polar organic solvent, no additional base being required when pyridine is used. However, if a solvent mixture of dichloromethane/DMF is used, it is recommended to add a pyridine base such as pyridine, triethyl amine or ethyl diisopropyl amine in order to chemically scavenge protons released during the reaction. The mixing ratio of dichloromethane to pyridine or DMF is not critical, but a ratio of 1 to 3 parts by volume of dichloromethane per part by volume of pyridine of DMF, respectively, is commonly used.

The nucleotide (13) obtained from reaction scheme 4 is dissolved in pyridine or DMF/base and a solution of the chlorocarbonic acid ester is added dropwise thereto to adjust the reaction mixture at the appropriate reaction temperature. The molar ratio of nucleoside to chlorocarbonic acid ester may be adjusted to 1:1 in accordance with stoichiometry. In addition, an excess of chlorocarbonic ester may be added in such an amount that the molar ratio of nucleoside to chlorocarbonic acid ester is 1:1 to 1:2.

After completion of the reaction (after about 5 to 6 hours), the nucleoside of an embodiment of the invention may be isolated and purified by known methods, for example, by dilution with dichloromethane, washing out any, drying of the organic phase, concentration of the solution or crystallization followed by silica gel chromatography. In this way, it is possible to obtain a nucleoside derivative having high purity in yield of about 70 to 80%.

According to another embodiment of the invention, it is possible to introduce a phosphite amide group of the following formula:

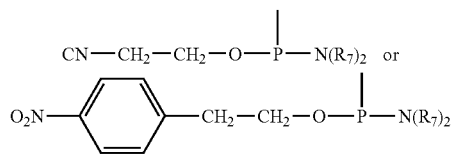

wherein $R_7$'s may be the same or different from each other and are independently a linear or branched alkyl radical having 1 to 4 carbon atoms, into the 3' position ($R_3$ position) of the nucleoside derivative by known methods.

In general, this reaction with the suitable phosphines is carried out in the presence of 1H tetrazole as a catalyst in a solvent mixture of dichloromethane and acetonitrile at 0 to 25° C. The phosphine may be used in a 1.5 to 3-fold molar excess, while the molar ratio of phosphine to 1H tetrazole is adjusted to 2 to 4:1.0. The quantitative ratio of dichloromethane to acetonitrile is not very critical and may be 1:1 to 4:1.

More detailed embodiments of the present invention will be described through the following specific Experimental Examples.

Experimental Example 1

Synthesis of Halonitrophenyl Compound (a) Synthesis of 3-acetyl-trifluoroacetylaminobenzene 10 mmol of 3'-aminoacetophenone as a starting material was dissolved in a methanol solvent in a 100 mL round-bottomed flask and 1.2 equivalents (eq) of methyl trifluoroacetate was added dropwise thereto over 30 minutes at room temperature, and subsequently the reaction mixture was stirred for 2 hours. After the completion of the reaction was confirmed by TLC, a small amount of water was added to terminate the reaction. Then, the solvent was removed under reduced pressure. The residue was dissolved in 50 mL of ethyl acetate and washed twice with 30 mL of water, dried over anhydrous sodium sulfate, and distilled under reduced pressure to obtain the desired 3-acetyl-trifluoroacetylaminobenzene (85%) as a brown oil.

Rf=0.39 (Hexane/EtOAc=1/1), 1H NMR (300 MHz, CDCl$_3$) δ 7.70 (s, 1H, NH), 7.33-7.14 (m, 4H, aromatic), 2.13 (s, 3H)

(b) Synthesis of 3-acetyl-4-nitro-aminobenzene 10 mmol of 3-acetyl-trifluoroacetylaminobenzene as a starting material was slowly added dropwise to 20 mL of concentrated H$_2$SO$_4$ at −20° C. and the reaction mixture was stirred 30 minutes. Then, nitric acid was slowly added dropwise thereto over 10 minutes. The reaction mixture was continuously stirred for 2 hours. When the reaction was completed, ice water was poured into the reaction mixture. The reaction mixture was extracted twice with 50 mL of ethyl acetate. The organic layer was washed with a solution of sodium hydrogen carbonate and dried over anhydrous sodium sulfate. The ethyl acetate was then distilled off under reduced pressure to give an impure product. The impure produce was added to concentrated NH$_4$OH and stirred at 50° C. for 1 hour. The reaction mixture was evaporated on a rotary evaporator and extracted with EtOAc and water, and purified by silica gel column chromatography (hexane/EtOAc=3/1) to obtain the desired 3-acetyl-4-nitro-aminobenzene as a brown solid (54%).

Rf=0.25 (Hexane/EtOAc=3/1), 1H NMR (300 MHz, CDCl$_3$) δ 7.95 (m, 1H), 6.44 (m, 2H), 3.99 (br, 2H, NH2), 2.11 (s, 3H)

(c) Synthesis of 3-acetyl-4-nitro-bromobenzene 10 mmol of 3-acetyl-4-nitro-aminobenzene as a starting material was added to 100 mL of HBr/H$_2$O (1/2, v/v) and a sodium nitrite solution was slowly added dropwise thereto in an ice bath. The reaction mixture was stirred at 60° C. for 2 hours. When the reaction was completed, the precipitate was filtered off. The filtrate was neutralized with 1N NaOH, extracted with EtOAc, dried over anhydrous sodium sulfate, distilled under reduced pressure and purified by silica gel column chromatography (hexane/EtOAc=2/1) to obtain the desired 3-acetyl-4-nitro-bromobenzene as a yellow oil (75%).

Rf=0.31 (Hexane/EtOAc=2/1), 1H NMR (300 MHz, CDCl$_3$) δ 7.74 (d, 1H), 7.52 (d, 1H), 7.44 (dd, 1H), 2.11 (s, 3H)

(d) Synthesis of 1-(5-bromo-2-nitrophenyl)ethanol 10 mmol of 3-acetyl-4-nitro-bromobenzene was placed in a 100 mL two-neck round-bottomed flask and dissolved in 30 mL of a solvent (ether), and then sodium borohydride was slowly added dropwise thereto in an ice bath. The reaction mixture was stirred at room temperature for 2 hours. After the completion of the reaction was confirmed by TLC, 5 mL of water was added to terminate the reaction and the precipitate was filtered off. The filtrate was washed twice with 30 mL of a sodium chloride solution, dried over anhydrous sodium sulfate, distilled under reduced pressure and purified by silica gel column chromatography (hexane/EtOAc=2/1) to obtain the desired 1-(5-bromo-2-nitrophenyl)ethanol as a yellow oil (71%).

Rf=0.33 (hexane/EtOAc=1/3), 1H NMR (300 MHz, CDCl$_3$) δ 7.73 (d, 1H), 7.52 (d, 1H), 7.42 (dd, 1H), 6.15 (m, 1H), 1.79 (br, 1H), 1.62 (d, 3H)

Experimental Example 2

Synthesis of Palladium Coupling Derivative

(a) Synthesis of 1-(2-nitro-5-(2-(trimethylsilyl)ethynyl)phenyl)ethanol 10 mmol of nitrobromophenyl as a starting material was placed in a round-bottomed flask and dissolved in 30 mL of DMF, and then 5% Pd(OAc)2, 1 eq of LiCl and 1.2 eq of KOAc were slowly added dropwise the reaction solution. Then, 1.5 eq of acetylene was added to the reaction solution.

The whole reaction was carried out at room temperature and the completion of the reaction was confirmed by TLC. When the reaction was completed, water was added to quench the reaction. The reaction product was extracted with 50 mL of NH$_4$Cl (aqueous, saturated) and 50 mL of EtOAc, and the desired compound was isolated as an organic layer, washed once with a sodium chloride solution, dried over anhydrous sodium sulfate, and the solvent was distilled off under reduced pressure to obtain the target compound. The target compound was finally purified by silica gel column chromatography (hexane/EtOAc=2/1) to obtain the desired compound (66%).

Rf=0.35 (hexane/EtOAc=1/3), IR (neat) 2190, 2950 cm$^{-1}$, 1H NMR (300 MHz, CDCl3) δ 7.69 (d, 1H), 7.51 (d, 1H), 7.43 (dd, 1H), 6.15 (m, 1H), 1.74 (br, 1H), 1.62 (d, 3H), 0.19 (s, 9H)

(b) Synthesis of 3-(3-(1-hydroxyethyl)-4-nitrophenyl)prop-2-yn-1-ol 3-(3-(1-Hydroxyethyl)-4-nitrophenyl)prop-2-yn-1-ol was obtained in the same manner as in (a) of Experimental Example 2.

Rf=0.31 (hexane/EtOAc=1/2), IR (neat) 2120 cm$^{-1}$, 1H NMR (300 MHz, CDCl$_3$) δ 7.69 (d, 1H), 7.51 (d, 1H), 7.43 (dd, 1H), 4.18 (d, 2H), 6.18 (m, 1H), 2.92 (br, 2H), 1.75 (br, 1H), 1.62 (d, 3H)

(c) Synthesis of 6-(3-(1-hydroxyethyl)-4-nitrophenyl)hex-5-ynentrile 6-(3-(1-Hydroxyethyl)-4-nitrophenyl)hex-5-ynenitrile was obtained in the same manner as in (a) of Experimental Example 2.

Rf=0.45 (Hexane/EtOAc=1/3), IR (neat) 2122, 2260 cm$^{-1}$, 1H NMR (300 MHz, CDCl$_3$) δ 7.71 (d, 1H), 7.52 (d, 1H), 7.43 (dd, 1H), 3.91 (m, 1H), 3.21 (d, 3H), 2.52 (t, 2H) 2.38 (t, 2H), 1.85 (m, 2H)

(d) Synthesis of 1-(5-(2-cyclohexylethynyl)-2-nitrophenyl)ethanol 1-(5-(2-Cyclohexylethynyl)-2-nitrophenyl)ethanol was obtained in the same manner as in (a) of Experimental Example 2.

Rf=0.42 (Hexane/EtOAc=1/1), IR (neat) 2115, 3120 cm$^{-1}$, 1H NMR (300 MHz, CDCl$_3$) δ 7.71 (d, 1H), 7.52 (d, 1H), 7.43 (dd, 1H), 3.91 (m, 1H), 2.37 (m, 1H), 1.88-1.24 (m, 13H)

(e) Synthesis of 1-(5-(3-aminoprop-1-ynyl)-2-nitrophenyl)ethanol 1-(5-(3-Aminoprop-1-ynyl)-2-nitrophenyl)ethanol was obtained in the same manner as in (a) of Experimental Example 2.

Rf=0.31 (hexane/EtOAc=1/5), IR (neat) 2110, 3300 cm$^{-1}$, 1H NMR (300 MHz, CDCl$_3$) δ 7.69 (d, 1H), 7.51 (d, 1H), 7.45 (dd, 1H), 6.21 (m, 1H), 3.33 (d, 2H), 3.21 (d, 3H), 1.45 (s, 2H)

(f) Synthesis of 1-(5-(3-(ethylthio)prop-1-ynyl)-2-nitrophenyl)ethanol 1-(5-(3-(Ethylthio)prop-1-ynyl)-2-nitrophenyl)ethanol was obtained in the same manner as in (a) of Experimental Example 2.

Rf=0.35 (hexane/EtOAc=1/2), IR (neat) 2130 cm$^{-1}$, 1H NMR (300 MHz, CDCl$_3$) δ 7.69 (d, 1H), 7.51 (d, 1H), 7.45 (dd, 1H), 6.02 (m, 1H), 3.78-3.65 (m, 4H), 1.79 (t, 3H), 1.62 (d, 3H)

(g) Synthesis of 1-(5-(2-cyclohexenylethynyl)-2-nitrophenyl)ethanol 1-(5-(2-Cyclohexenylethynyl)-2-nitrophenyl)ethanol was obtained in the same manner as in (a) of Experimental Example 2.

Rf=0.33 (hexane/EtOAc=1/2), IR (neat) 1632, 2101, 2952 cm$^{-1}$, 1H NMR (300 MHz, CDCl$_3$) δ 7.72 (d, 1H), 7.51 (d, 1H), 7.44 (dd, 1H), 6.17 (t, 1H), 5.98 (m, 1H), 2.13 (m, 4H), 1.63 (d, 3H), 1.59 (m, 4H)

(h) Synthesis of 1-(2-nitro-5-(2-(pyridin-2-yl)ethynyl)phenyl)ethanol 1-(2-Nitro-5-(2-(pyridin-2-yl)ethynyl)phenyl)ethanol was obtained in the same manner as in (a) of Experimental Example 2.

Rf=0.34 (hexane/EtOAc=1/3), IR (neat) 1647, 3058 cm$^{-1}$, 1H NMR (300 MHz, CDCl$_3$) δ 8.62 (dd, 1H), 7.72 (d, 1H), 7.55 (m, 2H), 7.45 (dd, 1H), 7.34 (dd, 1H), 7.17 (m, 1H), 5.99 (m, 1H), 1.74 (br, 1H), 1.62 (d, 3H),

(i) Synthesis of 2-nitro-5-(2-phenylethynyl)phenyl)ethanol

2-Nitro-5-(2-phenylethynyl)phenyl)ethanol was obtained in the same manner as in (a) of Experimental Example 2.

Rf=0.45 (hexane/EtOAc=2/1), IR (neat) 1602, 1112, 3063 cm$^{-1}$, 1H NMR (300 MHz, CDCl$_3$) δ 7.69 (d, 1H), 7.51 (d, 1H), 7.44 (m, 3H), 7.27 (m, 3H), 6.02 (m, 1H), 1.62 (d, 3H), 1.69 (s, 1H)

(j) Synthesis of 1-(2-nitro-5-(2-p-tolylethynyl)phenyl)ethanol 1-(2-Nitro-5-(2-p-tolylethynyl)phenyl)ethanol was obtained in the same manner as in (a) of Experimental Example 2.

Rf=0.35 (hexane/EtOAc=1/2), IR (neat) 1619, 2122, 3069 cm$^{-1}$, 1H NMR (300 MHz, CDCl$_3$) δ 7.66 (m, 2H), 7.51 (d, 1H), 7.32 (dd, 2H), 5.98 (m, 1H), 2.32 (s, 3H), 1.93 (br, 1H), 1.61 (d, 3H)

(k) Synthesis of 1-(2-nitro-5-(2-(thiophen-3-yl)ethynyl)phenyl)ethanol 1-(2-Nitro-5-(2-(thiophen-3-yl)ethynyl)phenyl)ethanol was obtained in the same manner as in (a) of Experimental Example 2.

Rf=0.35 (hexane/EtOAc=1/2), IR (neat) 1413, 2925, 3113 Cm$^{-1}$, 1H NMR (300 MHz, CDCl$_3$) δ 7.75 (d, 1H), 7.54 (d, 1H), 7.42 (dd, 1H), 7.21 (m, 1H), 6.77 (m, 2H), 5.98 (m, 1H), 3.25 (d, 3H), 1.79 (br, 1H)

(l) Synthesis of 1-(5-(2-(naphthalen-1-yl)ethynyl)-2-nitrophenyl)ethanol 1-(5-(2-(Naphthalen-1-yl)ethynyl)-2-nitrophenyl)ethanol was obtained in the same manner as in (a) of Experimental Example 2.

Rf=0.35 (hexane/EtOAc=1/2), IR (neat) 1391, 1589, 3085 cm$^{-1}$, 1H NMR (300 MHz, CDCl$_3$) δ 7.94 (d, 1H), 7.81 (d, 1H), 7.65 (m, 2H), 7.53-7.25 (m, 6H), 5.92 (m, 1H), 1.63 (d, 3H), 1.71 (br, 1H)

Experimental Example 3

Synthesis of Oxycarbonyl Chloride 10 mmol of 1-(2-nitro-5-ethynyl)phenyl)ethanol as a starting material and 1.5 eq of triethylamine were placed in a two-neck round-bottom flask and dissolved in a THF solution, and then 3 eq of trichloromethyl chloroformate dissolved in THF was added dropwise thereto at 0° C. over 5 minutes. The reaction mixture was stirred at 0° C. for 1 hour and the precipitate formed was filtered off. The filtrate was subjected to fractional distillation to obtain the desired compound (nitrophenyl chloroformate derivative).

Experimental Example 4

Preparation of Nucleoside Having Photolabile Protective Group of Formula 1

A photolabile protective group and a nucleoside with a base were reacted. First, 10 mmol of the nucleoside with a base was distilled three times under reduced pressure with dry pyridine on a rotary evaporator. Then, the nucleoside was dissolved in 20 mL of pyridine and 10.2 mmol of the nitrophenyl chloroformate derivative was slowly added dropwise thereto at −10° C. under N$_2$ (g). Subsequently, 0.1 eq of DMAP dissolved in 5 mL of pyridine was added thereto and the reaction mixture was stirred with a stirring bar for 5 hours. The completion of the reaction was confirmed by TLC. When the reaction was completed, pyridine was removed under reduced pressure. The residue was dissolved in 50 mL of EtOAc, and washed once with 50 mL of NaHCO$_3$ (aqueous, saturated) and once with 30 mL of NaCl (aqueous, saturated). The organic layer was dried over Na$_2$SO$_4$, distilled under reduced pressure, and then purified by purified by silica gel column chromatography to obtain the desired compound (photolabile protective deoxynucleoside).

(a) Synthesis of 5'-O-[1-(2-nitro-5-(2-(trimethylsilyl)ethyl)phenyl)ethanol]2'-deoxythymidine 10 mmol of 2'-deoxythymidine as a starting material was distilled three times under reduced pressure with dry pyridine on a rotary evaporator. Then, the 2'-deoxythymidine was dissolved in 20 mL of pyridine and 10.2 mmol of the nitrophenyl chloroformate derivative was slowly added dropwise thereto at −10° C. under N$_2$ (g). Subsequently, 0.1 eq of DMAP dissolved in 5 mL of pyridine was added thereto and the reaction mixture was stirred with a stirring bar for 5 hours. The completion of the reaction was confirmed by TLC. When the reaction was completed, pyridine was removed under reduced pressure. The residue was dissolved in 50 mL of EtOAc, and washed once with 50 mL of NaHCO$_3$ (aqueous, saturated) and once with 30 mL of NaCl (aqueous, saturated). The organic layer was dried over Na$_2$SO$_4$, distilled under reduced pressure, and then purified by purified by silica gel column chromatography (hexane/EtOAc=1/4) to obtain the desired compound (69%, white solid, 5'-O-[1-(2-nitro-5-(2-(trimethylsilyl)ethynyl)phenyl)ethanol]2'-deoxythymidine).

Rf=0.31 (hexane/EtOAc=1/4), 1H NMR (300 MHz, CDCl$_3$) δ 11.23 (br, 1H), 7.72 (d, 1H), 7.65 (s, 1H), 7.59 (d, 1H), 7.44 (dd, 1H), 5.24 (s, 1H), 5.12 (s, 1H), 4.32 (s, 1H), 6.01 (m, 1H), 3.69 (m, 1H), 3.58 (m, 2H), 2.25 (m, 2H), 1.81 (s, 3H), 1.62 (d, 3H), 0.19 (s, 9H)

(b) Synthesis of 5'-O-[1-(2-nitro-5-(2-trimethylsilyl)ethynyl)phenyl)ethanol]2'-deoxythymidine-3'-O-(β-cyanoethoxy-N,N-diisopropyl)phosphoramidite 10 mmol of 5'-O-[1-(2-nitro-5-(2-(trimethylsilyl)ethynyl)phenyl)ethanol]2'-deoxythymidine as a starting material was dissolved in 30 mL of a solvent (CH$_3$Cl$_2$) under nitrogen, and 1.5 eq of diisopropylethylamine was added thereto and 1.2 eq of bis(diisopropylamino)-β-cyanoethoxyphosphane was slowly added dropwise to the reaction mixture at room temperature. The completion of the reaction was confirmed by TLC. When the reaction was completed, the reaction product was washed once with 30 mL of water and once with 30 mL of NaCl (aqueous, saturated), dried over anhydrous sodium sulfate, and then purified by purified by silica gel column chromatography (Hex/EtOAc/Et$_3$N=1/1/0.01) to obtain the desired compound (5'-O-[1-(2-nitro-5-(2-(trimethylsilyl)ethynyl)phenyl)ethanol]2'-deoxythymidine-3'-O-(β-cyanoethoxy-N,N-diisopropyl)phosphoramidite) as a white solid (71%).

Rf=0.35 (Hexane/EtOAc=1/1), 1H NMR (300 MHz, CDCl$_3$) δ 8.41 (br, 1H), 7.73 (d, 1H), 7.45 (s, 1H), 7.35 (d, 1H), 7.27 (dd, 1H), 5.95 (m, 1H), 4.59-4.13 (m, 4H), 3.84 (m, 1H), 3.75 (m, 1H), 3.61 (m, 3H), 2.61 (m, 2H), 2.51 (m, 1H), 2.13 (m, 1H), 1.91 (s, 3H), 1.62 (d, 3H), 1.21 (m, 12H), 0.19 (s, 9H)

Experimental Example 5

Preparation of Linker Having Photolabile Protective Group of Formula 1

Synthesis of 2-(2-(2-(2((2-cyanoethoxy)(diisopropylamino)phosphinooxy)ethoxy)ethoxy)ethoxy)ethyl 1-(2-nitro-5-(2-trimethylsilyl)ethynyl)phenyl)ethyl Carbonate 10 mmol of 2-(2-(2-(2-hydroxyethoxy)ethoxy)ethoxy) ethyl 1-(2-nitro-5-(2-(trimethylsilyl)ethynyl)phenyl)ethyl carbonate as a starting material was dissolved in 30 mL of a solvent (CH$_2$Cl$_2$) under nitrogen, and 1.5 eq of diisopropylethylamine was added thereto and 1.2 eq of bis(diisopropylamino-β-cyanoethoxyphosphane was slowly added dropwise to the reaction mixture at room temperature. The completion of the reaction was confirmed by TLC. When the reaction was completed, the reaction product was washed once with 30 mL of water and once with 30 mL of NaCl (aq., sat.), dried over anhydrous sodium sulfate, and then purified by purified by silica gel column chromatography (Hex/EtOAc/Et3N=1/2/0.01) to obtain 2-(2-(2-(2-((2-cyanoethoxy)(diisopropylamino)phosphinooxy)ethoxy)ethoxy) ethoxy)ethyl 1-(2-nitro-5-(2-trimethylsilyl)ethynyl)phenyl) ethyl carbonate as a white solid (72%).

Rf=0.35 (Hexane/EtOAc=1/2), 1H NMR (300 MHz, CDCl$_3$) δ 7.72 (d, 1H), 7.44 (d, 1H), 7.36 (dd, 1H), 5.95 (m, 1H), 4.25 (m, 2H), 3.78 (m, 2H), 3.59 (m, 14H), 2.59 (t, 2H), 1.60 (d, 3H), 0.19 (s, 9H)

Irradiation Experiments

1. Execution

Photolabile protective deoxynucleoside derivatives were dissolved in acetonitrile/H$_2$O (95/5 (v/v)) at a concentration of 100 μM, irradiated by means of an Hg (Xe) ARC lamp (200 W) with the wavelength of 365 nm for 10 sec, 20 sec, 30 sec, 40 sec, 50 sec and 1 min, and then the deprotection was monitored by HPLC. Irradiation was carried out in quartz cells and analyzed by HPLC (Varian MicroPak SP column (C18)) with time. The solvent was ACH:H$_2$O=1:1.5 and the flow rate was 1 mL/min.

Comparative Example 1 is deoxythymidine (dT) having methyl-6-nitroperonyloxycarbonyl (MeNPOC) as a photolabile protective group.

Comparative Example 2 is deoxythymidine (dT) having 3'-nitrophenylpropyloxycarbonyl (NPPOC) as a photolabile protective group.

Compound 1 to Compound 8 are compounds represented by the following formulae.

Compound 1 to Compound 8 are compounds wherein R$_1$'s in the formulae are each methyl, trimethysilyl, methanol, cyclohexyl, cyclohexenyl, phenyl, naphthalenyl or thiophenyl, and the respective structural formulae are the same as the following formulae:

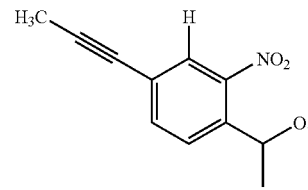

Compound 1

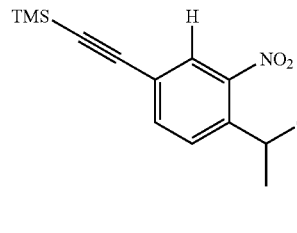

Compound 2

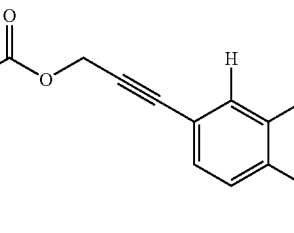

Compound 3

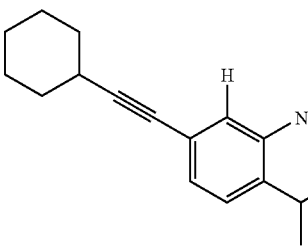

Compound 4

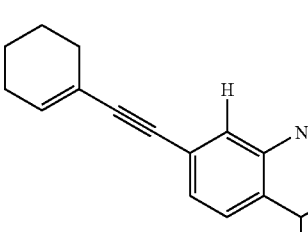

Compound 5

-continued

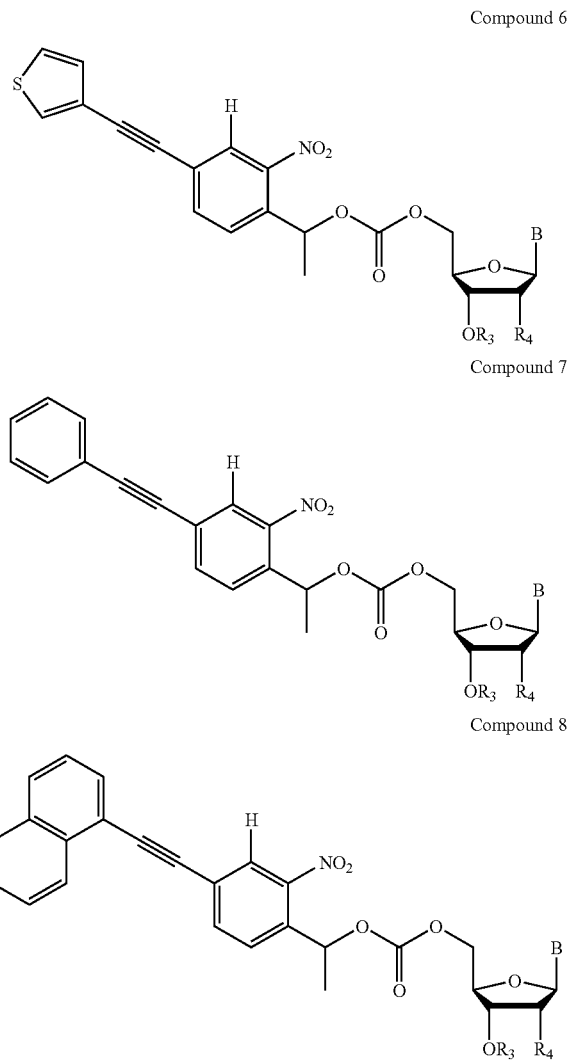

Compound 6

Compound 7

Compound 8

Compound 1 to Compound 8 are represented by the formulae wherein $R_2$ is a hydrogen atom; Y is

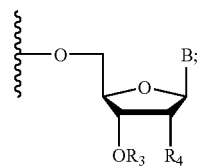

B is thymidine; $R_4$ is a hydrogen atom; and $R_3$ is

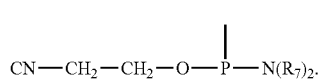

Figure 4:
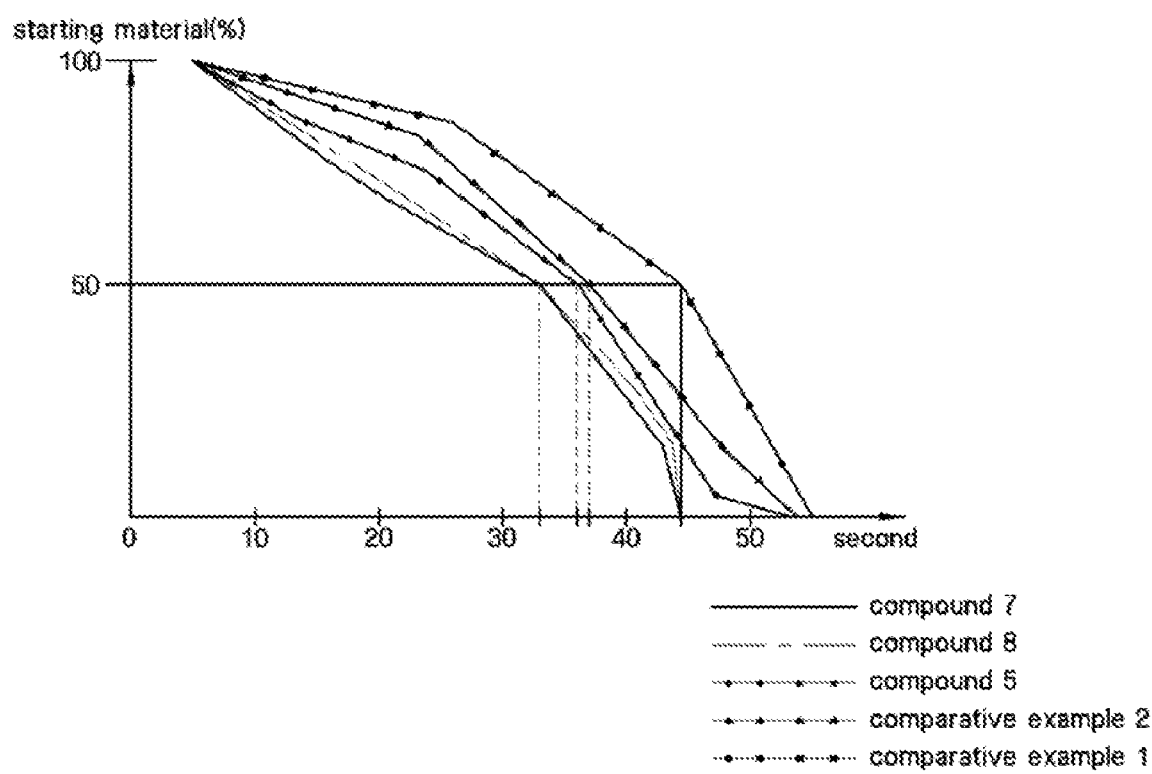
FIG. 4 is a graph analyzing the results of the irradiation experiments, according to an embodiment of the invention.

FIG. 4 is a graph analyzing the results of the irradiation experiments, and Table 1 shows numerical values of the results of the irradiation experiments and shows the results of the HPLC analysis with exposure time.

TABLE 1

Results of irradiation experiments

|    | Compound | Solvent (v/v) | Half-life ($t^{1/2}$, second) |
|----|----------|---------------|----------|
| 1  | Comparative Example 1 | $ACN/H_2O = 95/5$ | 44 |
| 2  | Comparative Example 2 | $ACN/H_2O = 95/5$ | 37 |
| 3  | Compound 1 | $ACN/H_2O = 95/5$ | 37 |
| 4  | Compound 2 | $ACN/H_2O = 95/5$ | 35 |
| 5  | Compound 3 | $ACN/H_2O = 95/5$ | 36 |
| 6  | Compound 4 | $ACN/H_2O = 95/5$ | 35 |
| 7  | Compound 5 | $ACN/H_2O = 95/5$ | 34 |
| 8  | Compound 6 | $ACN/H_2O = 95/5$ | 37 |
| 9  | Compound 7 | $ACN/H_2O = 95/5$ | 33 |
| 10 | Compound 8 | $ACN/H_2O = 95/5$ | 33 |

As shown from FIG. 4 and Table 1, a compound synthesized according to an embodiment of the present invention has improved photolytic degradation rate, as compared to the compounds that Comparative Example 1 (MeNPOC) and Comparative Example 2 (NPPOC), which have been widely used in the prior art as photolabile protective groups, are attached to nucleosides. In particular, Compound 7 and Compound 8 had the shortest half-change value.

Although exemplary embodiments of the present invention have been described, it will be apparent to those skilled in the art that various modifications and changes may be made thereto without departing from the scope and spirit of the invention. Therefore, it should be understood that the above embodiments are not limitative, but illustrative in all aspects.

As described above, the photolabile compound according to an embodiment of the present invention can be used in the production of the oligomer probe array. Since the compound represented by the formula and the substrate for an oligomer probe array to which the material represented by the formula is attached, are fast in the deprotection of the photolabile protective groups contained therein, the total reaction yield can be increased when they are used in the production of an oligomer probe array.

What is claimed is:

1. A photolabile compound represented by the following formula:

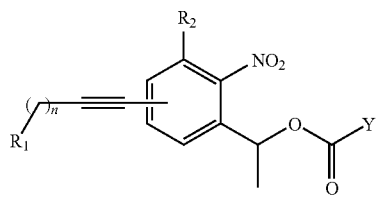

wherein $R_1$ is a methyl group, an amino group, a hydroxyl group, acetic ester group, a phenyl group, a diphenyl group, a trimethylsilyl group, a cyanide group, an azide group, a sulfur atom, a cycloalkyl group, a cycloalkenyl group or a heterocyclic group;

n is an integer from 1 to 8;

$R_2$ is a hydrogen atom or alkyl derivative; and

Y is a halogen atom, a hydroxyl group, a moiety represented by one of the following formulae:

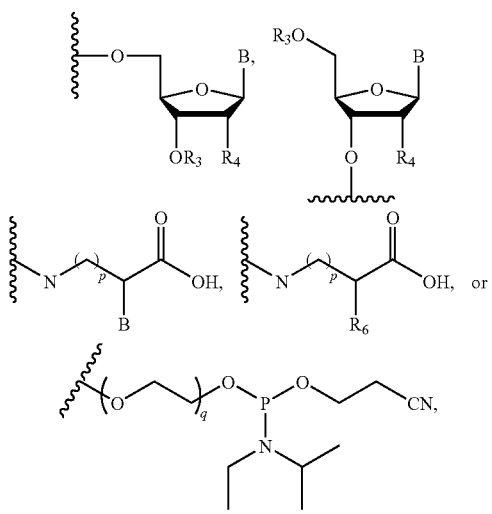

wherein B is adenine, cytosine, guanine, thymine or uracil;
  $R_3$ is a hydrogen atom, an amino group, an alkyl group or a phosphine group;
  $R_4$ is a hydrogen atom, a hydroxyl group, —$OR_5$ or —$SR_5$ wherein $R_5$ is an alkyl group, an alkenyl group, an acetal group or a silyl ether group;
  $R_6$ is an alkyl group, a phenyl group, or a sulfur atom;
  p is an integer from 0 to 5; and
  q is an integer from 0 to 10.

2. The photolabile compound of claim 1, wherein $R_1$ is methyl, trimethysilyl, an acetic ester group, cyclohexyl, cyclohexenyl, phenyl, naphthalenyl or thiophenyl.

3. The photolabile compound of claim 1, wherein Y is

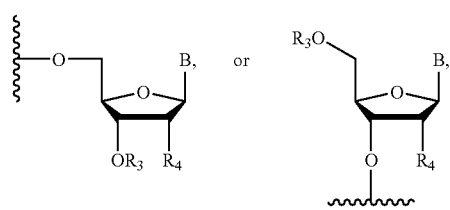

wherein
  B is adenine, cytosine, guanine, thymine or uracil;
  $R_3$ is a hydrogen atom, an amino group, an alkyl group or a phosphine group; and
  $R_4$ is a hydrogen atom, a hydroxyl group, —$OR_5$ or —$SR_5$ wherein $R_5$ is an alkyl group, an alkenyl group, an acetal group or a silyl ether group.

4. The photolabile compound of claim 3, wherein $R_3$ is a hydrogen atom or a phosphite amide group of the following formula:

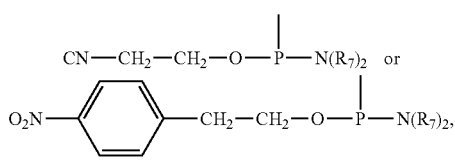

wherein $R_7$'s may be the same or different from each other and are independently a linear or branched alkyl radical having 1 top 4 carbon atoms.

5. The photolabile compound of claim 3, wherein $R_4$ is an O-methyl radical, O-ethyl radical, an O-allyl radical, an O-tetrahydropyranyl radical, an O-methoxytetrahydropyranyl radical or an O-t-butyldimethylsilyl radical.

6. The photolabile compound of claim 1, wherein Y is

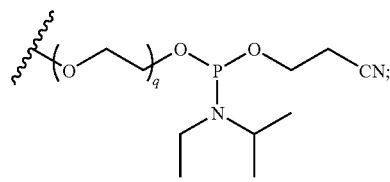

and q is an integer from 3 to 10.

7. A substrate for an oligomer probe array to which a material is directly attached or attached via a linker, the material being represented by the following formula:

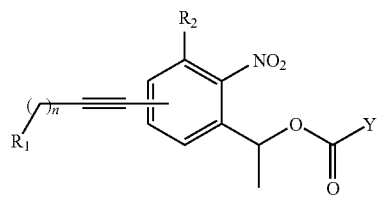

wherein
  $R_1$ is a methyl group, an amino group, a hydroxyl group, an acetic ester group, a phenyl group, a diphenyl group, a trimethysilyl group, a cyanide group, an azide group, a sulfur atom, a cycloalkyl group, a cycloalkenyl group or a heterocyclic group;
  n is an integer from 1 to 8;
  $R_2$ is a hydrogen atom or an alkyl derivative; and
  Y is a halogen atom, a hydroxyl group, or

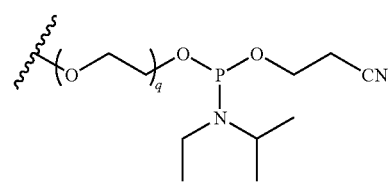

wherein q is an integer from 0 to 10.

8. The substrate for an oligomer probe array of claim 7, wherein the substrate is nylon, nitrocellulose, a plastic film, a silicon substrate and/or soda-lime glass.

9. The substrate for an oligomer probe array of claim 7, wherein the linker is a silane linker or nano particles.

* * * * *